US008735136B2

(12) United States Patent
Vinas Almenar et al.

(10) Patent No.: US 8,735,136 B2
(45) Date of Patent: May 27, 2014

(54) **BIOLOGICAL CULTURE OF A STRAIN OF THE *PSEUDOMONAS GRAMINIS* SPECIES, USE OF SAID CULTURE AS ANTAGONIST FOR BIOLOGICAL CONTROL OF PATHOGENIC BACTERIA, AND METHOD FOR TREATING FRUIT THAT COMPRISES THE STEP OF APPLYING, TO THE FRUIT, A PREPARATION THAT COMPRISES SAID CULTURE**

(75) Inventors: Immaculada Vinas Almenar, Lleida (ES); Maria Isabel Abadias Sero, Barcelona (ES); Josep Usall Rodie, Barcelona (ES); Neus Teixido Espasa, Barcelona (ES); Rosario Torres Sanchis, Barcelona (ES)

(73) Assignees: Institut de Recerca I Tecnologia Agroalimentaries (ES); Universitat de Lleida (ES)

( * ) Notice: Subject to any disclaimer, the term of this patent is extended or adjusted under 35 U.S.C. 154(b) by 0 days.

(21) Appl. No.: 13/976,291

(22) PCT Filed: Dec. 29, 2011

(86) PCT No.: PCT/US2011/070912

§ 371 (c)(1),
(2), (4) Date: Jun. 26, 2013

(87) PCT Pub. No.: WO2012/089887

PCT Pub. Date: Jul. 5, 2012

(65) Prior Publication Data

US 2013/0280226 A1 Oct. 24, 2013

(30) Foreign Application Priority Data

Dec. 29, 2010 (ES) .................................. 201031984

(51) Int. Cl.
*C12N 1/20* (2006.01)
*A01N 63/00* (2006.01)
(52) U.S. Cl.
USPC ..................................... 435/253.3; 424/93.47
(58) Field of Classification Search
None
See application file for complete search history.

(56) References Cited

U.S. PATENT DOCUMENTS 6,156,560 A 12/2000 Chun et al.

FOREIGN PATENT DOCUMENTS

WO WO01/15524 3/2001

OTHER PUBLICATIONS

PCT Search Report and Written Opinion for PCT/ES2011/070912, completed Apr. 2, 2012.
Leverentz, Britta, et al., "Biocontrol of the Food-Borne Pathogents *Listeria monocytogenes* and *Salmonella enterica* Serovar Poona on Fresh-Cut Apples with Naturally Occuring Bacterial and Yeast Antagonists", Feb. 2006, Applied and Environmental Microbiology, pp. 1135-1140.
Sharma, R. R., et al., "Biological Control of Postharvest Diseases of Fruits and Vegetables by Microbial Antagonists: A Review", May 2009, Biological Control, No. 50, pp. 205-221.
Alegre, I. et al., "Antagonistic effect of *Pseudomonas graminis* CPA-7 against foodborne pathogens in fresh-cut apples under simulated commercial conditions," Food Microbiology, 2013; 33:139-148.
Alegre, I. et al., "Control of foodborne pathogens on fresh-cut fruit by a novel strain of *Pseudomonas graminis*," Food Microbiology, 2013; 34:390-399.
Nunes et al., "Post-harvest biological control by *Pantoea agglomerans* (CPA-2) on Golden Delicious Apples," Journal of Applied Microbiology, 2002; 92: 247-255.
Reddy et al., "*Bacillus cecembensis* sp. nov., isolated from the Pindari glacier of the Indian Himalayas," IJSEM, 2008; 10 2330-2335.

*Primary Examiner* — Jennifer Pitrak McDonald
*Assistant Examiner* — Qing Xu
(74) *Attorney, Agent, or Firm* — Barnes & Thornburg LLP

(57) ABSTRACT

Substantially pure biological culture of a strain of the species *Pseudomonas graminis*, deposited with number CBS136973 at the depositary institution "Centraalbureau voor Schimmelcultures" (CBS) in Utrecht, Netherlands. Use of the CBS136973 culture as an antagonist for the biocontrol of foodborne pathogenic bacteria in fruit intended for human consumption. Method for treating the fruit which comprises the step of applying a preparation that comprises a culture of a strain of the species *Pseudomonas graminis*, deposited with number CBS136973 at the depositary institution "Centraalbureau voor Schimmelcultures" (CBS) in Utrecht, Netherlands, to the fruit. The application thereof makes it possible to reduce the growth of pathogens during the shelf life of the product, especially when the cold chain is broken.

20 Claims, 8 Drawing Sheets

BIOLOGICAL CULTURE OF A STRAIN OF THE *PSEUDOMONAS GRAMINIS* SPECIES, USE OF SAID CULTURE AS ANTAGONIST FOR BIOLOGICAL CONTROL OF PATHOGENIC BACTERIA, AND METHOD FOR TREATING FRUIT THAT COMPRISES THE STEP OF APPLYING, TO THE FRUIT, A PREPARATION THAT COMPRISES SAID CULTURE

CROSS-REFERENCE TO RELATED APPLICATIONS

This application is a national stage entry under 35 U.S.C. §371(b) of International Application No. PCT/ES2011/070912, filed Dec. 29, 2011, which claims the benefit of Spanish Patent Application Serial No. P201031984, filed Dec. 29, 2010, the disclosures of both of which are hereby incorporated herein by reference.

FIELD OF THE INVENTION

The present invention relates to a biological culture of a strain of the species *Pseudomonas graminis* and to the use of said strain as an antagonist for the biocontrol of foodborne pathogenic bacteria in fruit. It also relates to a method for treating fruit which comprises the step of applying a preparation that comprises said culture to the fruit.

BACKGROUND OF THE INVENTION

Fresh-cut fruit or minimally-processed fruit is a product that has recently appeared in markets. This fruit is subjected to a minimum processing which involves the washing, peeling, cutting, disinfection and packaging thereof in a passive or active modified atmosphere, to be finally stored under refrigeration conditions.

Fresh-cut fruit is a food product that is very susceptible to physical, chemical and biological alterations, which deteriorates at a higher rate than whole fruit. In fresh-cut fruit, respiration and metabolic processes are accelerated as a result of handling, for which reason it is essential to store the product in a modified atmosphere and keep it under refrigeration conditions.

Current regulations apply very strict microbiological criteria to fresh-cut fruit, in order to reduce to the minimum food toxi-infections or illnesses caused by the ingestion of fruit contaminated with bacteria such as *Salmonella* spp., *Listeria* spp. or *Escherichia coli* O157:H7 types.

Currently, in order to guarantee the safety of minimally-processed food products, treatments that involve washing the fruit with water with added sodium hypochlorite are usually applied. These treatments reduce the microbial load of the products, but have the disadvantage that they may leave a chlorine residue which facilitates the formation of substances that may be carcinogenic. Moreover, the treatment with hypochlorite does not prevent the growth of microorganisms during storage of the fruit or during the shelf life of the product.

The biocontrol of foodborne pathogenic bacteria in minimally processed products is a very desirable alternative to treatments with sodium hypochlorite. However, in order for this alternative to be viable, it is essential to find antagonistic microorganisms that are effective against any of the three aforementioned types of pathogenic bacteria (*Salmonella* spp., *Listeria* spp. and *Escherichia coli* O157:H7), both at room temperature and under refrigeration and modified atmosphere conditions. Moreover, it is desirable for these antagonists to be innocuous for both humans and vegetables, since, otherwise, they could harm the consumers or the treated product.

In the state of the art, antagonists have been disclosed for the biocontrol of foodborne pathogenic bacteria in fruit ("*Biological control of postharvest decays of apple can prevent growth of Escherichia coli O157:H7 in apple wounds*", Janisiewicz, W. et al. JOURNAL OF FOOD PROTECTION 62 (12): 1372-1375. 1999, and "*Biocontrol of the food-borne pathogens Listeria monocytogenes and Salmonella enterica serovar Poona on fresh-cut apples with naturally occurring bacterial and yeast antagonists*", Leverentz, B. et al. APPLIED AND ENVIRONMENTAL MICROBIOLOGY 72 (2): 1135-1140. 2006).

However, the antagonists used do not belong to the species *Pseudomonas graminis* and, moreover, none of them is effective against any of the microorganisms *Salmonella* spp. *Listeria* spp. and *Escherichia coli* O157:H7 either at room temperature or under refrigeration conditions.

SUMMARY DESCRIPTION OF THE INVENTION

A first objective of the present invention is to provide a substantially pure biological culture of a new strain of the species *Pseudomonas graminis* deposited with number CBS136973 at the depositary institution "Centraalbureau voor Schimmelcultures (CBS) in Utrecht, Netherlands.

A second objective is to provide a substantially pure biological culture of a new strain of the species *Pseudomonas graminis* deposited with number CBS136973, to be used as an antagonist for the biocontrol of foodborne pathogenic bacteria in fruit intended for human consumption.

A third objective of the present invention consists of the use of the aforementioned biological culture of the new strain as an antagonist for the biocontrol of foodborne pathogenic bacteria in fruit intended for human consumption.

A fourth objective involves a method for treating fruit which comprises the step of applying a preparation that comprises the aforementioned biological culture of the new strain to the fruit.

It has been observed that the isolated new strain shows great effectiveness as an antagonist against foodborne pathogenic bacteria in fruit, for a wide range of pathogens and fruits, at room temperature, in a modified atmosphere and under refrigeration conditions. The application thereof makes it possible to reduce the growth of pathogens during the useful life of the product, especially when the cold chain is broken.

In the present invention, foodborne pathogenic bacteria are understood to mean pathogenic bacteria that produce food toxi-infections or illnesses caused by the ingestion of contaminated foodstuffs, for example, fruit contaminated with pathogenic bacteria of the *Salmonella* spp., *Listeria* spp. or *Escherichia coli* O157:H7 types.

The new strain of the species *Pseudomonas graminis* (Behrendt et al. 1999[1]) was isolated from the surface of a "Golden Delicious" apple by means of washing with sterile water, followed by immersion in saline-peptone solution (peptone, 1 g/l; NaCl, 0.85 g/l), sonication in an ultrasound bath for 10 min and planting the washing liquid in NYDA culture medium (Nutrient broth, 8 g/l; yeast extract, 5 g/l; dextrose, 10 g/l, and agar, 15 g/l), and subsequent incubation at 25° C. for 3 days.

The new strain culture has been deposited by one of the applicants, in accordance with the specifications of the Budapest Treaty on the recognition of the deposit of microorganisms for purposes of patent procedure, at the international depositary authority "Centraalbureau voor Schimmelcultures (CBS)", with headquarters at Uppsalalaan 8, 3584 CT Utrecht, Netherlands. The deposit number assigned was CBS136973.

Isolate CBS136973 was identified by the partial sequencing of the region 16S rRNA: *Pseudomonas* sp., and by the full sequencing of the region 16S rRNA: *Pseudomonas graminis* (Behrendt et al., 1999[1]).

Morphological and Biochemical Characteristics of the New Strain

Strain CBS136973 is a gram-negative, non-spore-forming, oxidase-negative, catalase-positive, mobile, aerobic *bacillus*. In plates, the colonies are yellow, with a circular shape and whole edges.

Strain CBS136973 has the biochemical characteristics listed in Table 1 and is phenotypically differentiated from other *Pseudomonas* species by the tests shown in Table 2.

The growth temperature ranges between 5° C. and 30° C., with the optimum ranging between 25° C. and 30° C. It does not grow at 33° C. or 0° C.

Growth on plates may be performed in NA culture medium (Nutrient Agar: 5 g/l Tryptone, 3 g/l meat extract, 15 g/l agar), TSA (Tryptic soy broth: 15 g/l tryptone, 5.0 g/l soy peptone, 5.0 g/l sodium chloride and 15 g/l agar, pH 7.3) or NYDA (Nutrient broth: 8 g/l; yeast extract, 5 g/l; dextrose, 10 g/l and agar, 15 g/l).

Growth in liquid may be performed in TSB culture medium (Tryptone soy broth: 17.0 g/l pancreatic digest of casein, 3.0 g/l enzymatic digest of soybean meal, 5.0 g/l sodium chloride, 2.5 g/l dipotassium hydrogen phosphate, 2.5 g/l glucose, pH 7.3). NB medium (Nutrient broth: 10 g/l tryptone, 5 g/l meat extract, 5 g/l sodium chloride, pH 7.2) may also be used.

The growth of strain CBS136973 in TSB or NB medium under aerobic conditions, under stirring and at a temperature ranging between 25° C. and 30° C., reaches a maximum population size at 20-24 h of incubation (generally between 1.9 and 2.9×10$^9$ colony-forming units (cfu)/ml), without there being large differences between the two culture media.

TABLE 1

Enzymatic tests of the API 20 NE biochemical strips - Identification system for bacteria of the Biomerieux label. Results after 24 h and 48 h at 30° C.

| TEST | ACTIVE COMPONENTS | Enzymatic reactions | Result 24 h | Result 48 h |
|---|---|---|---|---|
| NO$_3$ | Potassium nitrate | Reduction of nitrates into nitrites | − | nd |
| | | Reduction of nitrates into nitrogen | − | nd |
| TRP | L-tryptophan | Formation of indol (TRyPtophan) | − | nd |
| GLU | D-glucose | Fermentation (GLUcose) | − | nd |
| ADH | L-arginine | Arginine Dihydrolase | − | − |
| URE | Urea | Urease | − | − |
| ESC | Aesculin Ferric citrate | Hydrolysis(β-glucosidase) (aESCulin) | + | + |
| GEL | Gelatin(bovine origin) | Hydrolysis (protease) (GELatin) | − | − |
| PNG | 4-nitrophenyl-βD-galactopyranoside | β-galactosidase (Para-NitroPhenyl-βD-Galactopyranosidase) | + | + |
| GLU | D-glucose | Assimilation (GLUcose) | + | + |
| ARA | L-arabinose | Assimilation (ARAbinose) | + | + |
| MNE | D-mannose | Assimilation (MaNnosE) | −/w | + |
| MAN | D-mannitol | Assimilation (MANnitol) | v | + |
| NAG | N-acetyl-glucosamine | Assimilation (N-Acetyl-Glucosamine) | − | v |
| MAL | D-maltose | Assimilation (MALtose) | v | v |

TABLE 1-continued

Enzymatic tests of the API 20 NE biochemical strips - Identification system for bacteria of the Biomerieux label. Results after 24 h and 48 h at 30° C.

| TEST | ACTIVE COMPONENTS | Enzymatic reactions | Result 24 h | Result 48 h |
|---|---|---|---|---|
| GNT | Potassium gluconate | Assimilation (potassium GlucoNaTe) | + | + |
| CAP | Capric acid | Assimilation (CAPric acid) | v | + |
| ADI | Adipic acid | Assimilation (ADIpic acid) | − | − |
| MLT | Malic acid | Assimilation (MaLaTe) | + | + |
| CIT | Trisodium citrate | Assimilation (trisodium CITrate) | + | + |
| PAC | Phenylacetic acid | Assimilation (phenylACetic acid) | − | − |

(+ positive, − negative, w weak, v variable, nd not determined)

TABLE 2

Phenotypical characteristics that differentiate strain CBS124167 from other species of *Pseudomonas*.

| Characteristic | Strain CBS124167 | *P. graminis*$^a$ | *P. lutea* | *P. rhizosphaerae* |
|---|---|---|---|---|
| Oxidase | −$^b$ | − | − | − |
| Growth at 6° C. | + | + | + | nd |
| Production of acid from glucose | − | − | − | − |
| Utilisation of erythritol | − | − | − | + |
| Utilisation of sorbitol | w | + | − | + |
| Utilisation of xylitol | − | v | + | − |
| Utilisation of melibiose | − | − | + | − |
| Utilisation of rhamnose | − | − | − | + |
| Hydrolysis of aesculin | + | + | + | − |
| Hydrolysis of gelatin | − | v | − | − |

$^a$The data for the reference species have been taken from Peix et al. (2003[3], 2004[4]) and Behrendt et al. (1999[1]).
$^b$+: positive; −: negative; w: weak; v: variable reaction between strains of the same species; nd: data not available Production of Anti-Microbial Substances Experiments were performed in order to determine whether strain CBS136973 produces anti-microbial substances. To this end, the strain was grown in TSB medium at 30° C., for 20-24 h. A fraction of the culture obtained was reserved, which was called "culture, CUL" and contained cells as well as culture medium and possible metabolites produced during growth. The rest was centrifuged at 8000 rpm for 10 min, at 10° C. The pH of the supernatant was adjusted to 6.5 and it was sterilised by filtration (0.22 μm), to obtain a "neutral cell-free supernatant, NCFS". The cellular fraction obtained following the centrifugation was re-suspended in sterile de-ionised water, centrifuged and washed two consecutive times in order to eliminate potential culture medium residues, to obtain only "cells, CEL".

The effectiveness of the following three fractions: CUL, NCFS and CEL, against several indicator cultures: *Escherichia coli* O157:H7, *Salmonella* spp., *Listeria innocua* and *Listeria monocytogenes* was determined under in vitro conditions. To this end, *Salmonella* spp. and *Escherichia coli* O157:H7 were made to grow in TSB medium and *Listeria* spp. was grown in TYSEB medium (TSB supplemented with 6 g/l of yeast extract) at 37° C., for 18-20 h. 50 μl of each of the cultures obtained were added to tubes containing 10 ml of TSB (*Salmonella* spp. and *Escherichia coli* O157:H7) or TYSEB medium (*Listeria* spp.) containing 7.5 g/l of agar and tempered at 45° C.

The content of each tube (medium+indicator culture) was deposited on plates containing 20 g/l meat extract, 20 g/l of glucose and 15 g/l of agar. Once they were solidified, 5 ml of the CUL, NCFS or CEL were deposited and the plates were incubated at 30° C., for 20 h; thereafter, the presence or absence of an inhibition halo was indicated.

No inhibition of growth of the indicator pathogens was observed in those treatments where the neutral cell-free supernatant was inoculated; thus, we may rule out the production of anti-microbial substances by strain CBS136973 under the assay conditions.

The in vivo effectiveness of the supernatant against *Escherichia coli* O157:H7, *Salmonella* spp. and *Listeria innocua* was also assayed in cut apple, and it was compared to the effectiveness of the cells. It was observed that the cell-free supernatants have no effect on the pathogen, and even favour the growth thereof after 2 days of storage at 20° C.

Phytopathogenicity

It was also determined whether or not strain CBS136973 is phytopathogenic, capable of producing a hypersensitivity reaction in tobacco leaves, according to the methodology of Noval et al. 1991[2]. To this end, a suspension of $10^9$ cfu/ml of the strain was prepared and injected in the veins of tobacco leaves using an insulin syringe. Water was used for the negative control and strain CPA-3 of *Pantoea ananatis* was used as a positive control, since this strain is phytopathogenic. The plants were kept at room temperature and periodical checks were performed in order to determine whether or not they presented symptoms of hypersensitivity, in the form of necrosis, yellowing of the infiltrated area or death of the leaves. No reaction was observed in the treated leaves, even with high doses of CBS136973 ($10^9$ cfu/ml). Therefore, strain CBS136973 is not phytopathogenic.

Survival in Gastric Juice Under Direct Contact and Inoculated in Apples

In order to evaluate the survival under direct contact, 50 ml of a suspension of $10^9$ cfu/ml of strain CBS136973 were added in a solution of simulated saliva and gastric juice (6.2 g/l NaCl, 2.2 g/l KCl, 0.22 g/l of $CaCl_2$ and 1.2 g/l $NaHCO_3$, 0.3 g/l pepsin; pH adjusted to 2.0, tempered at 37° C.) and incubated at 37° C., for 2 h. A sample was taken after 1 and 2 h. No viable cells of the strain of the present invention were detected, even after 10 min of contact.

In order to evaluate the survival in gastric juice of strain CBS136973 on apple, "Golden Delicious" apples were inoculated with strain CBS136973 at a dose of $10^7$ cfu/ml by means of bath immersion for 2 min. They were allowed to dry, packaged in polypropylene containers and sealed with a polypropylene film with a thickness of 35 µm and a permeability to $O_2$ and $CO_2$ of 3500 $cm^3/m^2$*day*atm at 23° C., and a permeability to water vapour of 0.9 $g/m^2$*day at 25° C. and 75% relative humidity, and stored at 5° C. After 0, 4, 7 and 14 days, 10 g were collected and subjected to a simulated gastric passage. To this end, they were mixed with 10 ml of artificial saliva solution (6.2 g/l NaCl, 2.2 g/l KCl, 0.22 g/l of $CaCl_2$ and 1.2 g/l $NaHCO_3$), tempered at 37° C. It was homogenised for 2 min and transferred to an Erlenmeyer flask with 80 ml of gastric juice (0.3 g/l pepsin; pH 2.0), and incubated at 37° C. for 2 h. Subsequently, the viable population of the strain was determined, by means of planting on NA medium.

No viable cells were observed in any of the samples analysed after 2 h of contact with the gastric juice. Therefore, it may be deduced that the strain of the present invention does not survive gastric passage. This is positive, since, even if the cells grow on the surface of the fruit during the storage thereof, said cells cannot cause any damage when the treated fruit is ingested, because they will not survive gastric transit. It is also worth mentioning that no references were found which relate the species *Ps. graminis* with cases of food toxi-infections.

Growth on the Fruit

It has been observed that strain CBS136973 is capable of growing on cut apples, peaches and melons at different temperatures, although the growth is much greater in melons, due to their lower acidity (higher pH). Growth has also been observed in fresh-cut apples under modified atmosphere conditions and under refrigeration temperature stored.

DETAILED DESCRIPTION OF THE INVENTION

It has been observed that strain CBS136973 is very effective against foodborne pathogenic bacteria in fruit, preferably, in fruit cut in pieces and, advantageously, against the microorganisms *Salmonella* spp., *Listeria* spp. and/or *Escherichia coli* O157:H7, which are the main ones in fruits and vegetables.

Thanks to this, strain CBS136973 may be used as an antagonist against any of said microorganisms, which favours the fulfillment of the microbiological criteria specified especially for fresh-cut fruit or minimally processed fruit, in order to prevent food toxi-infections or illnesses caused by the ingestion of fruit contaminated with bacteria belonging to *Salmonella* spp., *Listeria* spp. or *Escherichia coli* O157:H7 genera.

In particular, the effectiveness against *Salmonella* spp. has been observed for the species *Salmonella choleraesuis*, whereas the effectiveness against *Listeria* spp. has been observed for the species *Listeria monocytogenes* and *Listeria innocua*.

According to a first embodiment of the present invention, the strain of the present invention is used for biocontrol in fruit, preferably fruit cut in pieces, keeping the fruit at a temperature greater than 10° C., preferably a temperature equal to or greater than 20° C.

At room temperature, it has been observed that strain CBS136973 may slow down, and even reduce, the growth of any of the aforementioned microorganisms, even when these microorganisms are present on the fruit at a concentration equal to or greater than $10^3$ cfu/g, which is a very high concentration, difficult to find in real conditions.

This use is particularly advantageous since it makes it possible to control the growth of pathogens in those cases where the fruit storage temperature is not the adequate one, or the cold chain of the product is broken during the storage or transport thereof, for example, due to maintenance problems in the fruit refrigeration equipment. It is very important for the strain to be effective at room temperature, since this is the temperature where the pathogenic microorganism can grow the most and, consequently, the risk for the consumer increases.

According to a second embodiment, the strain of the present invention is used for biocontrol in fruit, for example fruit cut in pieces, keeping the fruit under refrigeration conditions. Refrigeration conditions are understood to mean keeping the fruit at a refrigeration temperature equal to or lower than 10° C., preferably equal to or lower than 5° C.

Surprisingly, the effectiveness of strain CBS136973 against any of the microorganisms *Salmonella* spp., *Listeria* spp. and *Escherichia coli* O157:H7 has also been demonstrated at refrigeration temperatures, which are those set by the producer or distributor for storage of the fruit.

According to a third embodiment, the strain of the present invention is used for biocontrol in fruit, preferably fresh-cut fruit, keeping the fruit in a modified atmosphere. Modified atmosphere is understood to mean an atmosphere with a gas composition different from that of air, in order to improve the fruit storage conditions.

The strain of the present invention also shows effectiveness when the fruit is packaged in a modified atmosphere for the storage thereof. Thanks to this, the strain may be used under habitual commercialisation conditions; consequently, it is also possible to guarantee food safety under the conditions of supermarket or displays.

Advantageously, said fruit is a fruit with a pH ranging between 3 and 7, for example, fruit such as apple, peach and/or melon.

It has been observed that the growth of *Salmonella* spp., *Listeria* spp. or *Escherichia coli* O157:H7 may occur in a wide range of fruits, despite the acidity conditions of certain fruits such as apples. It has also been observed that the growth of the aforementioned bacteria is very rapid in fruits that are less acidic, such as melons. However, thanks to the strain of the present invention, the growth of these pathogens may be controlled in a wide range of fruits.

As discussed in the description of the invention, one objective of the present invention is to provide a method for preparing fruit which comprises the step of applying a preparation that comprises the biological culture of the new strain CBS136973 to the fruit.

According to a preferred embodiment of said method, the fruit is cut in pieces prior to applying said preparation.

Preferably, the concentration of strain CBS136973 in said preparation is equal to or greater than the estimated pathogen concentration that the fruit, preferably the fresh-cut fruit, may contain.

According to one embodiment, the concentration of said strain in the preparation is equal to or greater than $10^5$ cfu/ml.

It has been observed that this concentration is effective against any of the three microorganisms *Salmonella* spp., *Listeria* spp. and/or *Escherichia coli* O157:H7, and at much higher concentrations than those whereat said microorganisms may be found in fresh-cut fruit in real conditions.

Advantageously, the concentration of said strain in the preparation is equal to or greater than $10^7$ cfu/ml.

It has been observed that this concentration guarantees a reduction in the pathogenic bacteria of at least two logarithmic units (two units of the base-10 logarithmic scale), regardless of the concentration of pathogenic bacteria in the fruit.

According to another embodiment, the method comprises the step of packaging the fruit once said preparation has been applied.

Advantageously, said method further comprises the step of providing a modified atmosphere to the fruit and/or the step of providing a refrigeration temperature to the fruit, for example, a temperature equal to or lower than 10° C., preferably a temperature equal to or lower than 5° C.

The modified atmosphere may be provided in a passive manner, for example, by packaging the product using plastic films with different permeabilities to gases, passively creating a favourable modified atmosphere as a result of the permeability of the container wall and factors such as respiration of the product and biochemical changes.

Packing the product in a modified atmosphere contributes to maintaining the freshness quality of the fresh-cut fruit for a longer period of time, which prolongs the shelf life of the product.

As previously discussed, the strain of the present invention is also effective under these conditions of packaging in a modified atmosphere.

Advantageously, said method for preparing the fruit, preferably fresh-cut fruit, comprises the step of applying an antioxidant to the fruit, prior to applying the suspension that contains the strain.

It has been observed that the strain of the present invention is not altered by the use of some antioxidant substances, for which reason said antioxidant substances may be used to delay oxidation of the fruit.

BRIEF DESCRIPTION OF THE FIGURES

In order to better understand what has been presented above, we attach some figures which represent, schematically and strictly for non-limiting purposes, the results of several embodiments.

In said drawings, the selected antagonists include those isolated from yeasts and bacteria such as CPA-1 (*Candida sake*), CPA-2 (*Pantoea* spp.), PN5 (*Bacillus* spp.), PN6 (*Pantoea* spp.), CPA-5 (*Pseudomonas* spp.), M174BAL2 (*Candida famata*), EL8 (*Pantoea* spp.), 128-M (*Pantoea* spp.), and C9P21 (*Pantoea* spp.).

Figure 1:
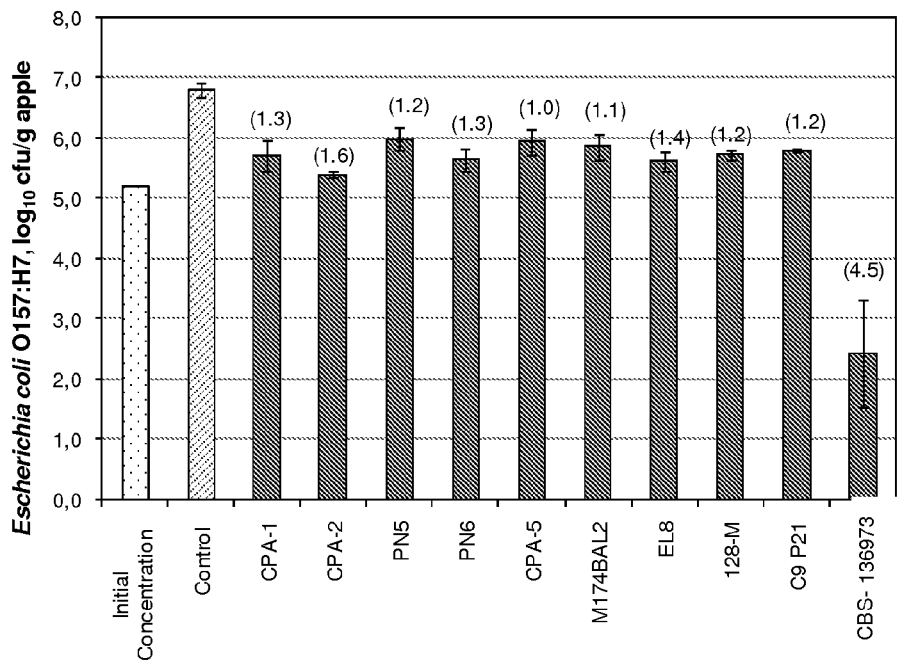

In said drawings,

FIG. 1 is a graphic representation that shows the population of *Escherichia coli* O157:H7 in apple cylinders after the inoculation (initial concentration), and after 2 days of incubation at 20° C. without an antagonist (control) and with 10 of the selected antagonists, which include the antagonist CBS136973. The values represent the mean of 6 values (2 assays with 3 repetitions each) and the bars represent the standard error. The numbers in brackets indicate the mean reduction obtained.

Figure 2:
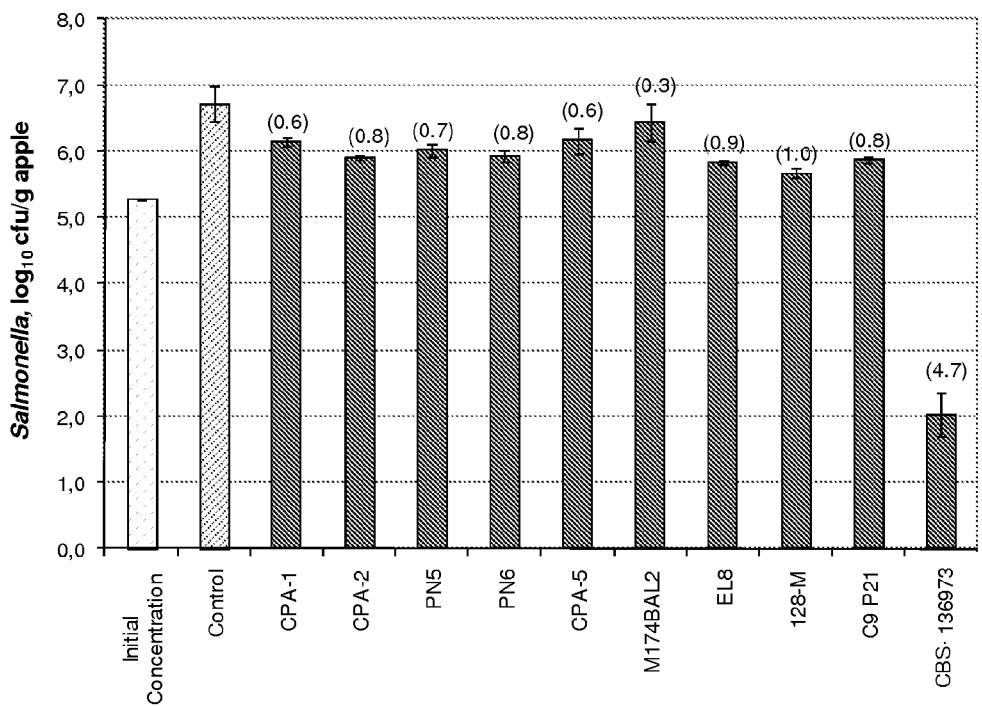

FIG. 2 is a graphic representation that shows the population of *Salmonella choleraesuis* BAA-709 in apple cylinders after the inoculation (initial concentration), and after 2 days of incubation at 20° C. without an antagonist (control) and with 10 of the selected antagonists, which include strain CBS136973. The values represent the mean of 6 values (2 assays with 3 repetitions each) and the bars represent the standard error. The numbers in brackets indicate the mean reduction obtained.

Figure 3:
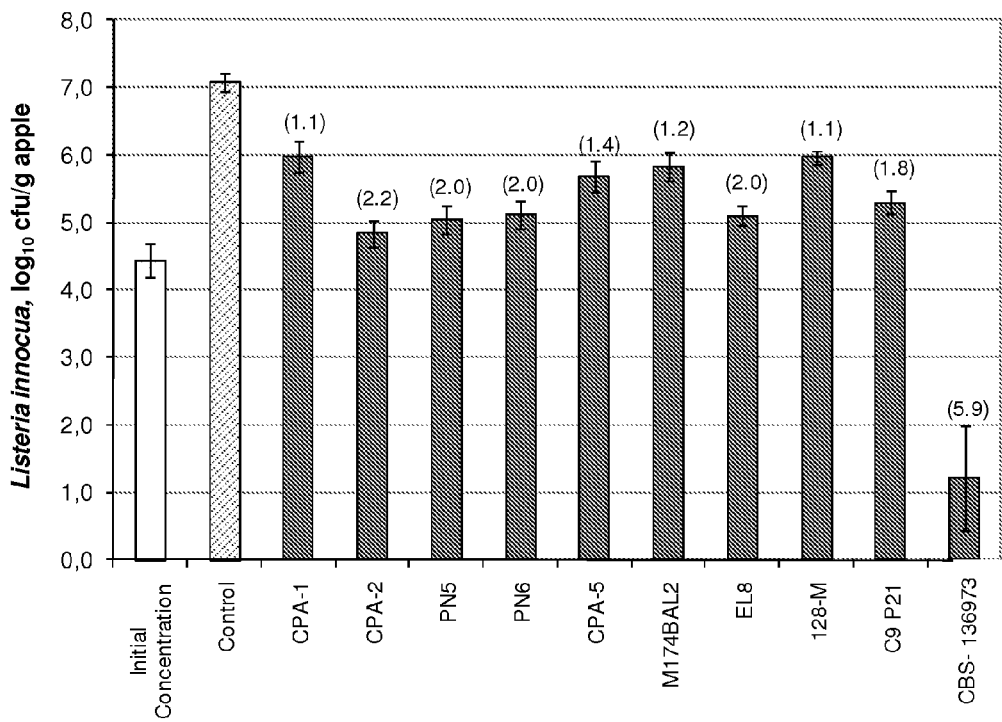

FIG. 3 is a graphic representation that shows the population of *Listeria innocua* CECT-910 in apple cylinders after the inoculation (initial concentration), after 2 days of incubation at 20° C. without an antagonist (control) and with 10 of the selected antagonists, which include strain CBS136973. The values represent the mean of 6 values (2 assays with 3 repetitions each) and the bars represent the standard error. The numbers in brackets indicate the mean reduction obtained.

Figure 4:
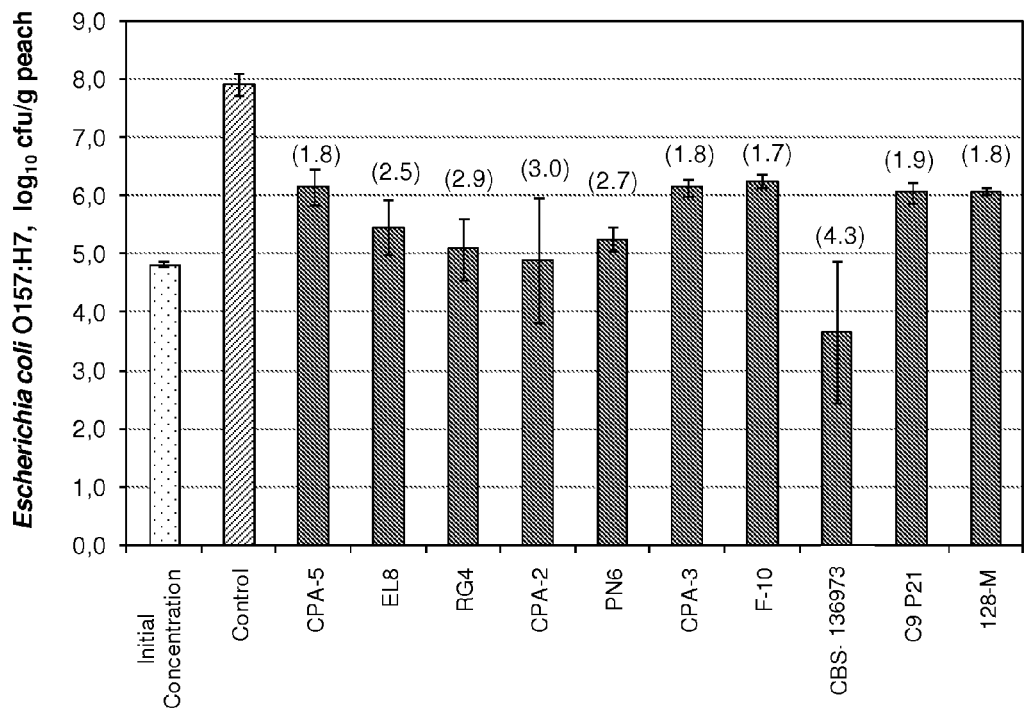

FIG. 4 is a graphic representation that shows the population of *Escherichia coli* O157:H7 in peach cylinders after the inoculation (initial concentration), after 2 days of incubation at 20° C. without an antagonist (control) and with 10 of the selected antagonists, which include strain CBS136973. The values represent the mean of 6 values (2 assays with 3 repetitions each) and the bars represent the standard error. The numbers in brackets indicate the mean reduction obtained.

Figure 5:
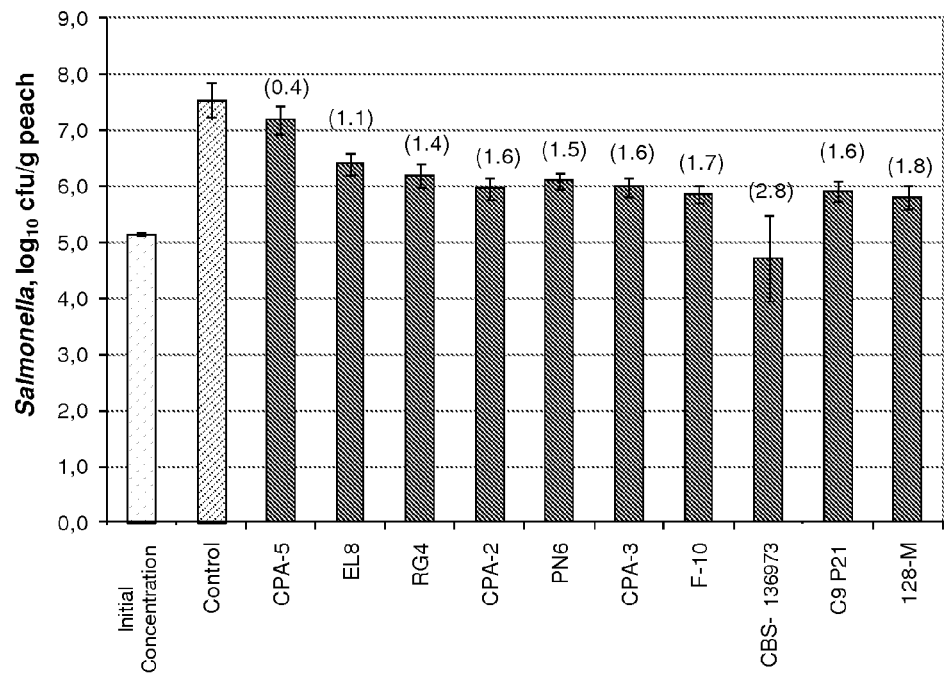

FIG. 5 is a graphic representation that shows the population of *Salmonella choleraesuis* BAA-709 in peach cylinders after the inoculation (initial concentration), and after 2 days of incubation at 20° C. without an antagonist (control) and with 10 of the selected antagonists, which include strain CBS136973. The values represent the mean of 6 values (2 assays with 3 repetitions each) and the bars represent the standard error. The numbers in brackets indicate the mean reduction obtained.

Figure 6:
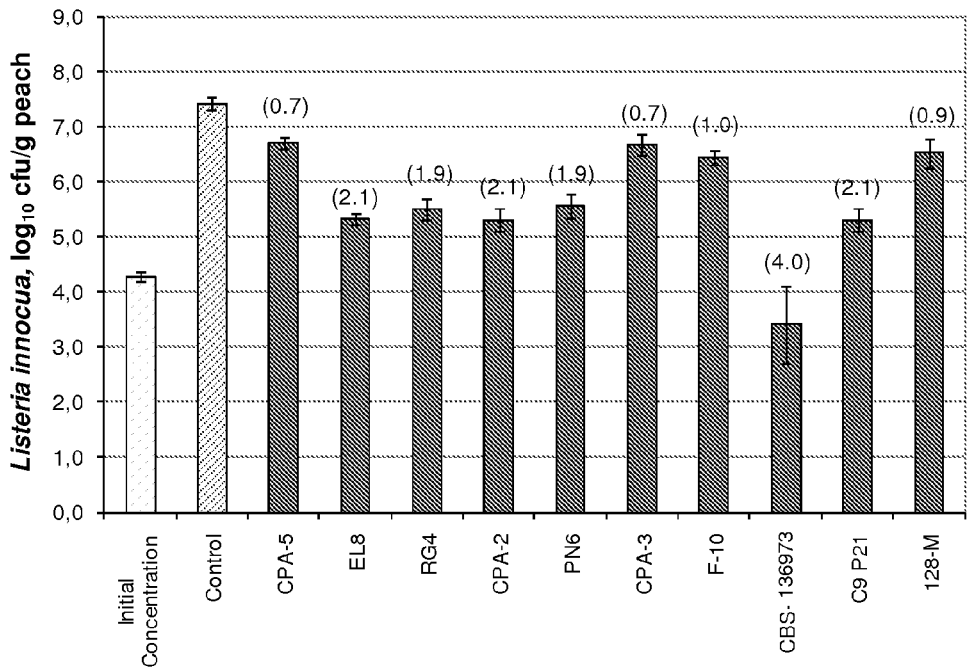

FIG. 6 is a graphic representation that shows the population of *Listeria innocua* CECT-910 in peach cylinders after the inoculation (initial concentration), and after 2 days of incubation at 20° C. without an antagonist (control) and with 10 of the selected antagonists, which include strain CBS136973. The values represent the mean of 6 values (2 assays with 3 repetitions each) and the bars represent the standard error. The numbers in brackets indicate the mean reduction obtained.

Figure 7:
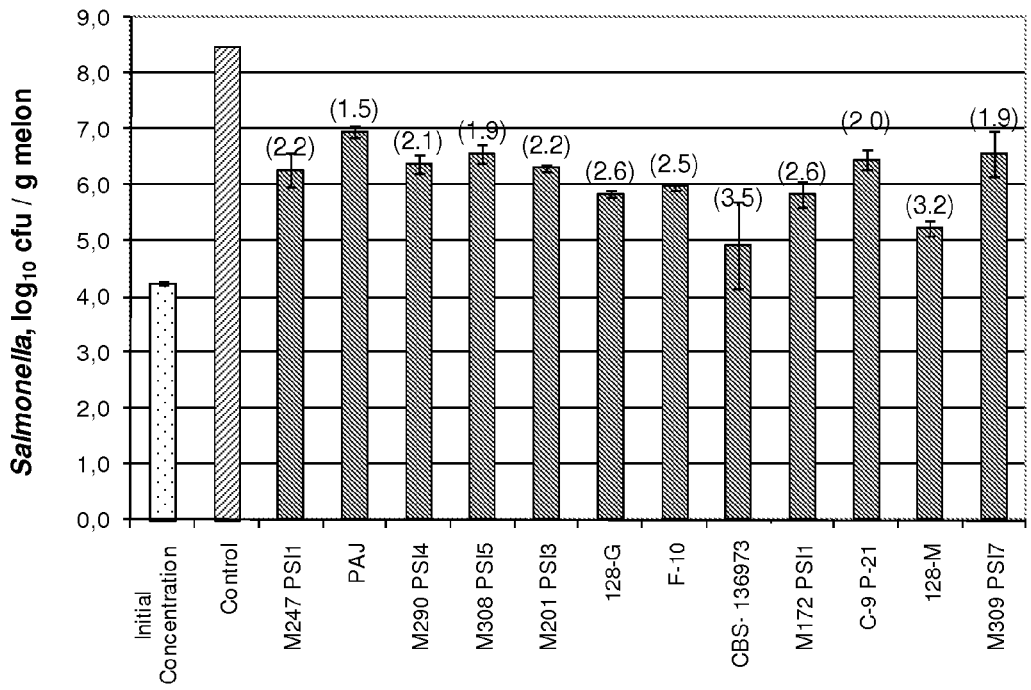

FIG. 7 is a graphic representation that shows the population of *Salmonella choleraesuis* BAA-709 in melon cylinders after the inoculation (initial concentration) and after 2 days of incubation at 20° C. without an antagonist (control) and with 12 of the selected antagonists, which include strain CBS136973. The values represent the mean of 6 values (2 assays with 3 repetitions each) and the bars represent the standard error. The numbers in brackets indicate the mean reduction obtained.

Figure 8:
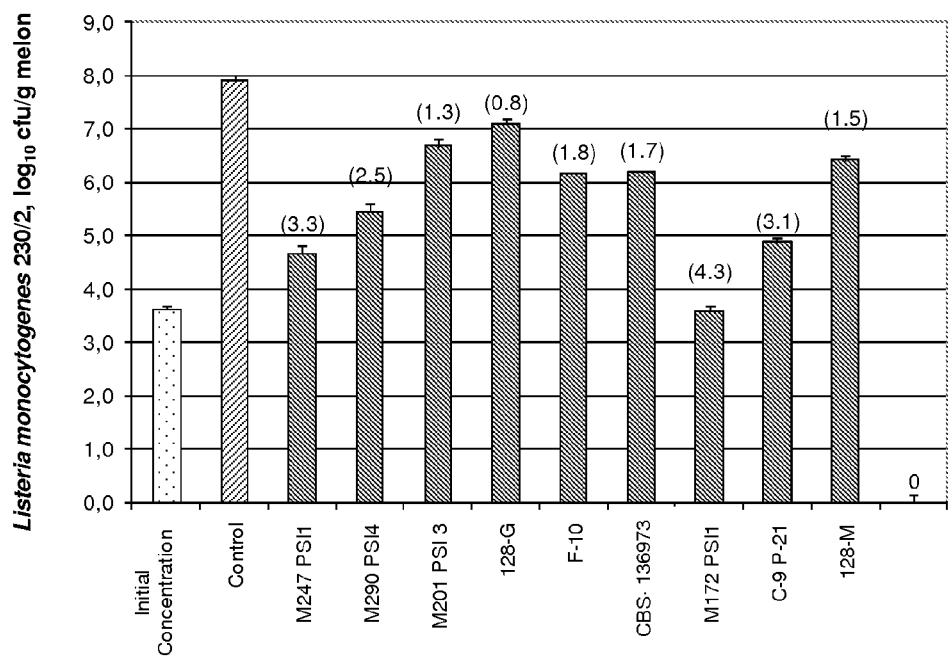

FIG. 8 is a graphic representation that shows the population of *Listeria monocytogenes* LM230/3 in melon cylinders after the inoculation (initial concentration), and after 2 days of incubation at 20° C. without an antagonist (control) and with 12 of the selected antagonists, which include strain CBS136973. The values represent the mean of 6 values (2 assays with 3 repetitions each) and the bars represent the standard error. The numbers in brackets indicate the mean reduction obtained.

Figure 9:
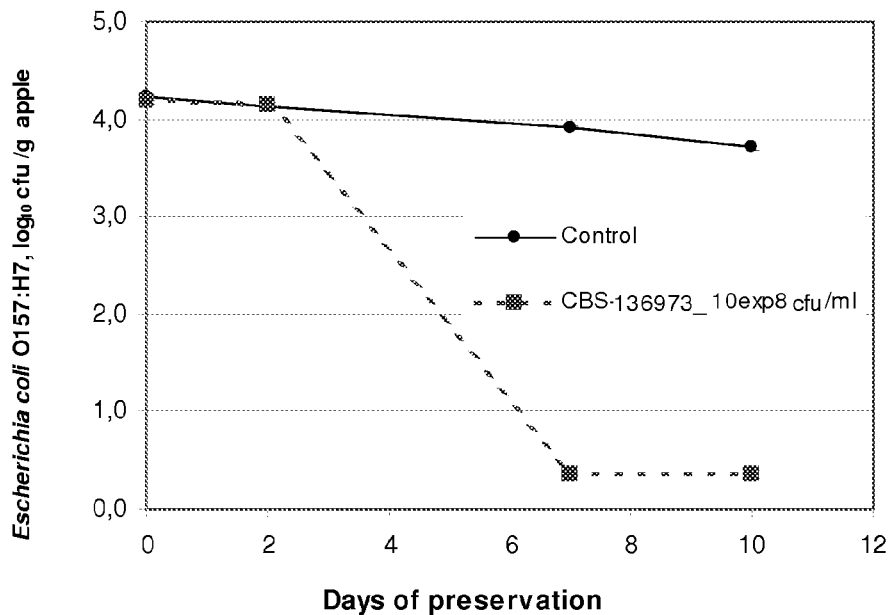

FIG. 9 is a graphic representation that shows of the population of *Escherichia coli* O157:H7 in apple cylinders coinoculated or not with a suspension of strain CBS136973 ($10^8$ cfu/ml) and stored at 5° C.

Figure 10:
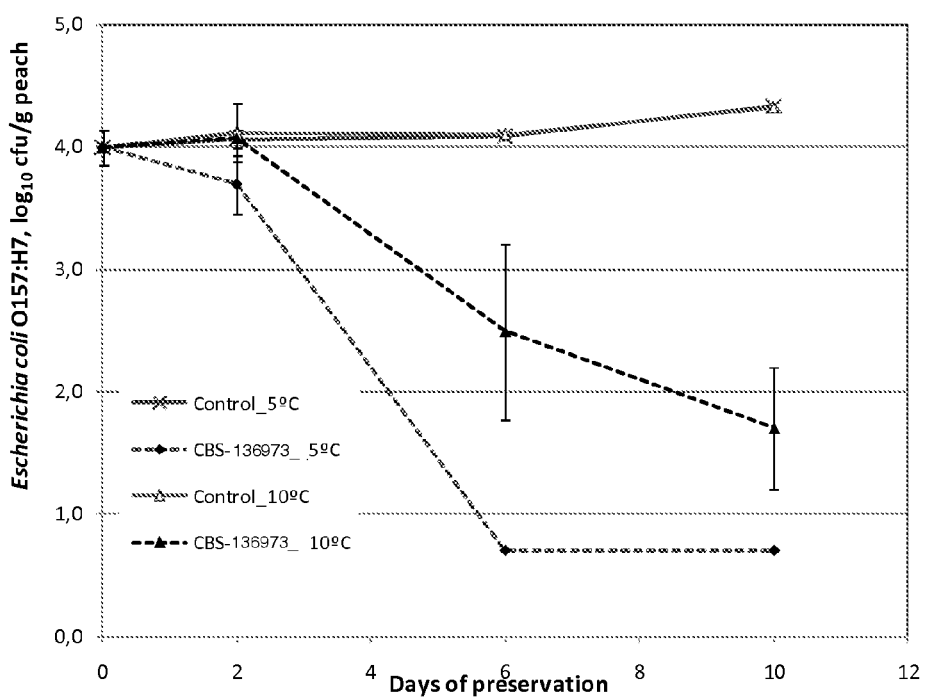

FIG. 10 is a graphic representation that shows the population of *Escherichia coli* O157:H7 in peach cylinders coinoculated or not with a suspension of strain CBS136973 ($10^8$ cfu/ml), and stored at 5° C. and at 10° C.

Figure 11:
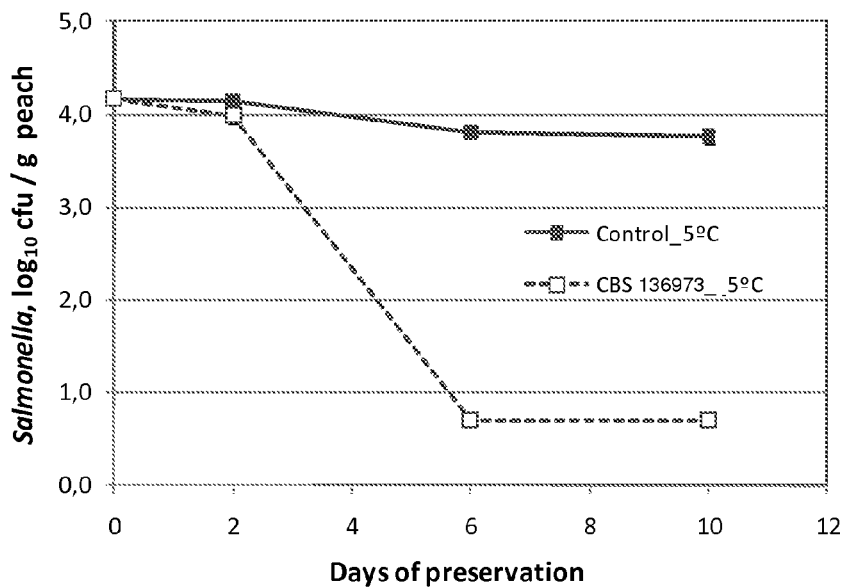

FIG. 11 is a graphic representation that shows the population of *Salmonella choleraesuis* BAA-709 in peach cylinders coinoculated or not with a suspension of strain CBS136973 ($10^8$ cfu/ml) and stored at 5° C.

Figure 12:
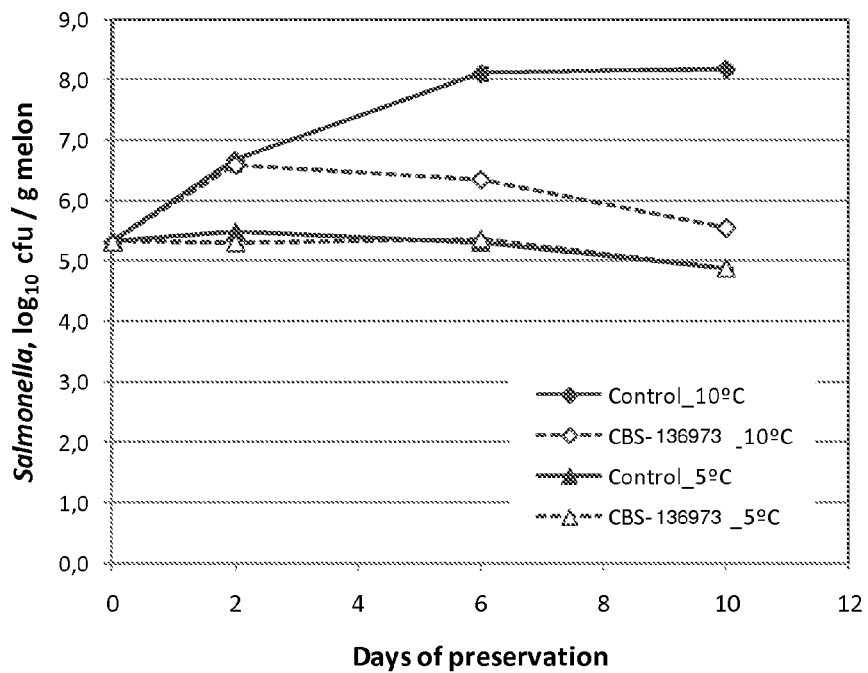

FIG. 12 is a graphic representation that shows the population of *Salmonella choleraesuis* BAA-709 in melon cylinders coinoculated or not with a suspension of strain CBS136973 ($10^8$ cfu/ml), and stored at 5° C. and at 10° C.

Figure 13:
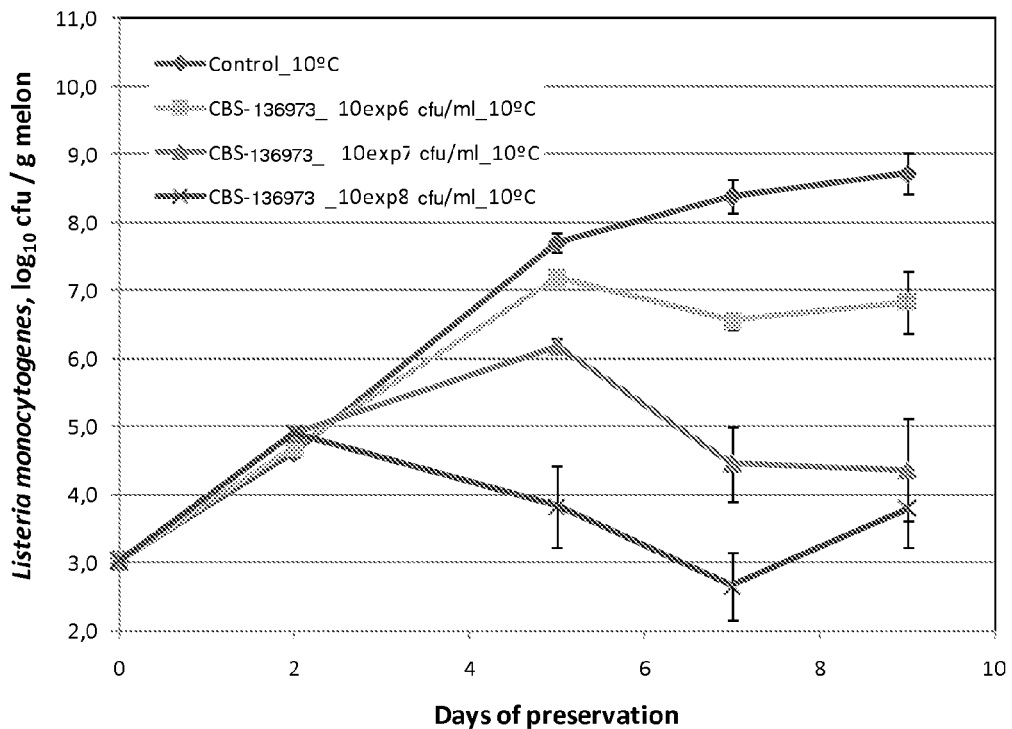

FIG. 13 is a graphic representation that shows of the population of a cocktail of strains of *Listeria monocytogenes* (CECT-4031, CECT-4032, CECT-933, CECT-940 and LM230/3) in melon cylinders coinoculated or not with strain CBS136973 at different concentrations and stored at 10° C.

Figure 14:
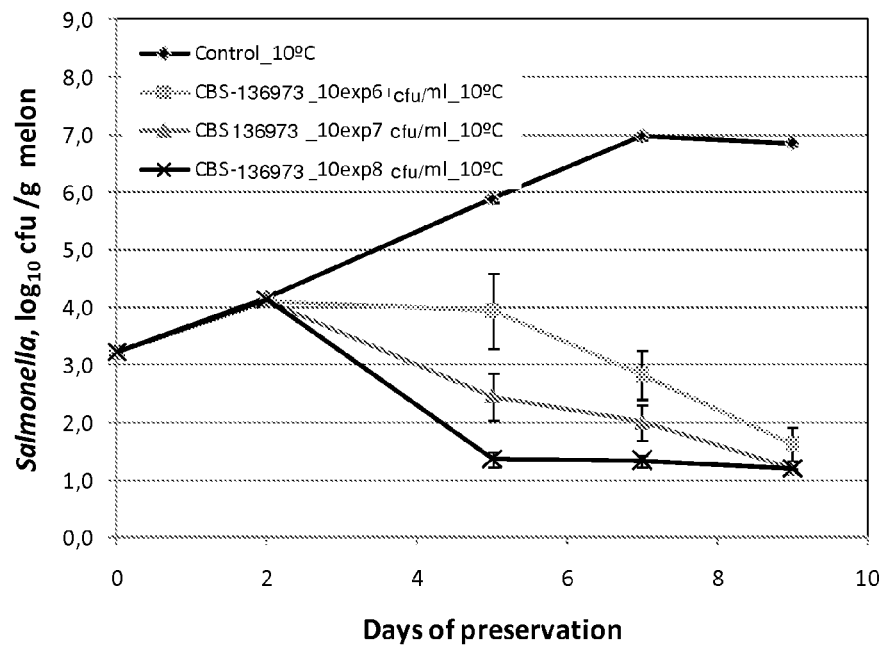

FIG. 14 is a graphic representation that shows the population of a cocktail of strains of *Salmonella choleraesuis* (BAA-707, BAA-709, BAA-710 and BAA-711) in melon cylinders coinoculated or not with strain CBS136973 at different concentrations and stored at 10° C.

Figure 15:
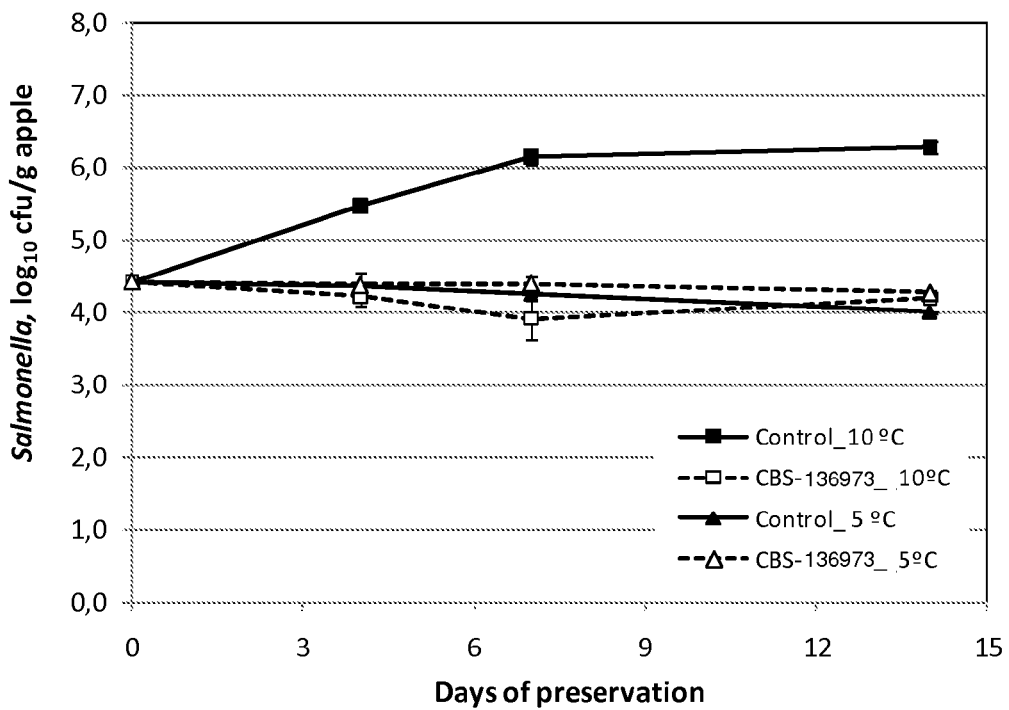

FIG. 15 is a graphic representation that shows of the population of a cocktail of strains of *Salmonella choleraesuis* (BAA-707, BAA-709, BAA-710 and BAA-711) in cut apple treated with antioxidant and inoculated or not with strain CBS136973 at $10^7$ cfu/ml, by means of immersion for 2 min, and stored in modified atmosphere packaging (MAP) at 5° C. and 10° C.

Figure 16:
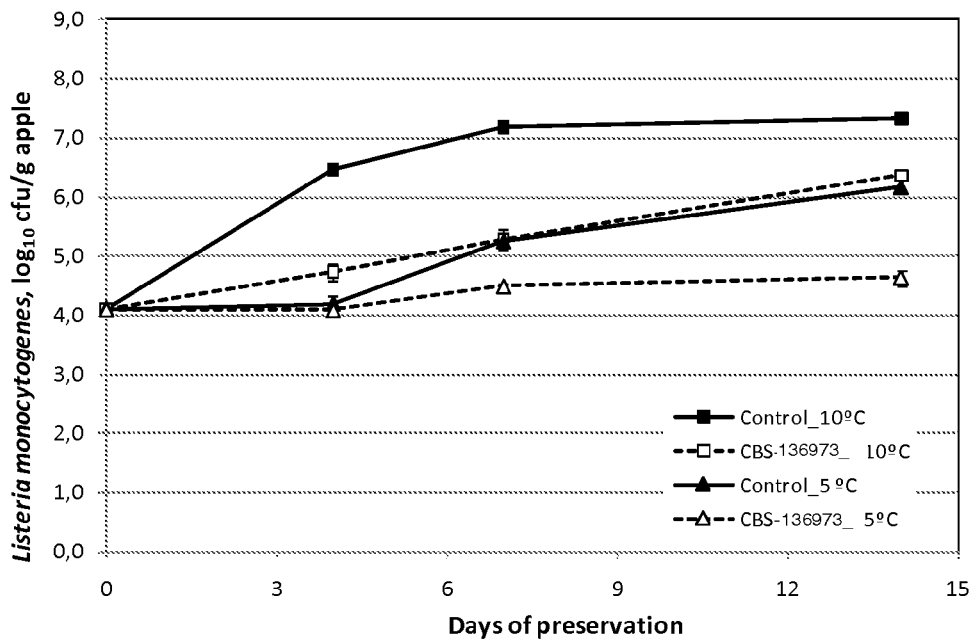

FIG. 16 is a graphic representation that shows of the population of a cocktail of strains of *Listeria monocytogenes* (CECT-4031, CECT-4032, CECT-933, CECT-940 and LM230/3) in cut apple treated with antioxidant and inoculated or not with strain CBS136973 at $10^7$ cfu/ml, by means of immersion for 2 min, and stored in modified atmosphere packaging (MAP) at 5° C. and 10° C.

DESCRIPTION OF THE EXAMPLES

Below we present different assays, which must be interpreted to be an auxiliary tool for a better understanding of the invention and not as limitations to the object thereof.

The antagonistic effect was assayed in different strains of the genera *Salmonella* and *Listeria*, and in a strain of *Escherichia coli* O157:H7. These pathogens are the major ones in fruits and vegetables. Table 3, attached, shows the strains of foodborne pathogenic microorganisms used in the assays.

Firstly, we describe the examples performed in order to demonstrate the effectiveness under laboratory conditions. Secondly, we describe the examples performed to demonstrate the effectiveness under conditions that simulate commercial production.

Assays Designed to Demonstrate the Effectiveness of the Strain CBS136973 Against the Major Foodborne Pathogens in Fresh-Cut Fruit Under Laboratory Conditions Below we describe a number of examples of assays performed under laboratory conditions which demonstrate the effectiveness of strain CBS136973 applied at different doses, in different fruits, at room temperature and under refrigeration conditions.

The strains of pathogenic microorganisms used in these assays were: *Listeria innocua* (CECT-910), *Escherichia coli* O157:H7 (NCTC-12900) and *Salmonella choleraesuis* (BAA-709, BAA-707, BAA-709, BAA-710 and BAA-711), and, in some cases, *Listeria monocytogenes* (CECT-4031, CECT-4032, CECT-933, CECT-940 and LM230/3) (see Table 3).

The fruits were previously disinfected by means of spraying with 70% ethanol. Subsequently, cylindrical pieces of the fruit to be assayed were prepared, by means of a punch, with the dimensions of 1.2 cm in diameter and 1 cm in height, which is approximately equivalent to 1 g of fruit. These pieces were introduced into sterile test tubes and inoculated with 15 µl of a suspension that contained the two microorganisms (pathogen and antagonist), a process called coinoculation. In the control treatment, the pathogen was added to a tube with 10 ml of sterile water (without an antagonistic microorganism). Following the coinoculation, the fruit was allowed to dry at room temperature. Subsequently, 3 tubes were collected, and the initial pathogen concentration was measured by means of seeding in specific culture media. The other tubes were stored at 20° C., 10° C. or 5° C., depending on the assay. After 2 days (assays at 20° C.), or 2-3 days, 5-7 days and 10 days (assays at 5° C. or 10° C.), the pathogen concentration per piece of fruit was once again determined in the samples with an antagonist (treatment with an antagonist) and in those that did not have an antagonist (control treatment). The concentration data were transformed to $\text{Log}_{10}$ cfc.

In order to calculate the pathogen growth reduction value, the following formula was used:

$$\text{Reduction Log}_{10} \text{ cfc} = \log_{10} C_{t\text{-control}} - \log_{10} C_{t\text{+antagonist}},$$

where:

$C_{t\text{-control}}$ is the pathogen concentration in the control treatment after "t" days of storage, and $C_{t\text{+antagonist}}$ is the pathogen concentration in the treatment with an antagonist after "t" days of storage.

Positive reduction values indicate that the growth of the pathogen on the fruit assayed in the presence of the antagonist is lower than the same without an antagonist. The higher the value, the greater the effectiveness against the pathogen studied.

In the assays at room temperature (20° C.), in order to obtain the suspension of strain CBS136973 and the other strains assayed, production in NYDA medium incubated at 25° C. for 48 h was used. Isolated colonies were taken, suspended in sterile de-ionised water and, from said suspension, another suspension was prepared, which was adjusted, by means of a spectrophotometer, to different transmittances (λ=420 nm) that correspond to the different concentrations of antagonists assayed ($10^5$ cfu/ml, $10^6$ cfu/ml, $10^7$ cfu/ml and $10^8$ cfu/ml).

In the assays under refrigeration conditions (5° C. or 10° C.), in order to obtain the suspension of strain CBS136973, production in a liquid medium was used. To this end, an Erlenmeyer flask was inoculated containing 50 mL of TSB and incubated at 30° C. for 20-24 h. It was centrifuged for 10 min at 10000 rpm and cells resuspended with 25 ml of sterile de-ionised water.

The pathogens were inoculated in tubes containing 10 ml of TSB medium (*Salmonella choleraesuis* BAA-707, BAA-709, BAA-710 and BAA-711, and *Escherichia coli* O157:H7) or TYSEB medium (*Listeria innocua* CECT-910 and *Listeria monocytogenes* CECT-4031, CECT-4032, CECT-933, CECT-940 and LM230/3), which were incubated at 37° C. for 20-24 h. Subsequently, they were centrifuged at 8000 rpm for 10 min and cells resuspended with 5 ml of saline solution (0.85 g/l of NaCl). By measuring the transmittance at 420 nm and a curve previously obtained in the laboratory for each of the pathogens, the estimated pathogen concentration was determined.

TABLE 3

List of strains of foodborne pathogenic microorganisms used in the assays.

| Culture collection | Species | Serovar | Nomenclature |
|---|---|---|---|
| ATCC BAA-707 | *Salmonella choleraesuis* subsp. *choleraesuis* (Smith) Weldin | Agona | BAA-707 |
| ATCC BAA-709 | *Salmonella choleraesuis* subsp. *choleraesuis* (Smith) Weldin | Michigan | BAA-709 |
| ATCC BAA-710 | *Salmonella choleraesuis* subsp. *choleraesuis* (Smith) Weldin | Montevideo | BAA-710 |
| ATCC BAA-711 | *Salmonella choleraesuis* subsp. *choleraesuis* (Smith) Weldin | Gaminara | BAA-711 |
| CECT-4031 | *Listeria monocytogenes* (Murray et al. 1926[8]) Pirie 1940 | 1a | CECT-4031 |
| CECT-4032 | *Listeria monocytogenes* (Murray et al. 1926[8]) Pirie 1940 | 4b | CECT-4032 |
| CECT-933 | *Listeria monocytogenes* (Murray et al. 1926[8]) Pirie 1940 | 3a | CECT-933 |
| CECT-940 | *Listeria monocytogenes* (Murray et al. 1926[8]) Pirie 1940 | 4d | CECT-940 |
| | *Listeria monocytogenes** | 1/2a | LM230/3 |
| CECT-910 | *Listeria innocua* | | *L. innocua* |
| NCTC-12900/ ATCC 700728 | *Escherichia coli* (Migula) Castellani and Chalmers serotype O157:H7 | | *E. coli* O157:H7 |

*Isolated from fresh-cut lettuce prepared at our laboratory (Abadias et al. 2008[5])
CECT: Spanish Type Culture Collection; ATTC: American Type Culture Collection; NCTC: National Collection of Type Cultures The pathogen concentrations assayed ranged between $10^5$ cfu/ml and $10^7$ cfu/ml. However, under real conditions, it is estimated that the $10^5$ cfu/ml pathogen concentration, which in the assays performed corresponds to $10^3$ cfu/g of product, is even a very high pathogen concentration (Salleh et al., 2003[6]; Nguz et al., 2005[7]); for this reason, the results obtained are presented under unfavourable/adverse conditions for strain CBS136973.

Example 1

Effectiveness of Strain CBS136973 Against Different Foodborne Pathogens on "Golden Delicious" Apples at 20° C.

FIGS. 1 to 3 show an example of the results obtained against strains of *Escherichia coli* O157:H7, *Salmonella choleraesuis* BAA-709 and *Listeria innocua* CECT-910, in "Golden Delicious" apples, comparing the effectiveness of strain CBS136973 with other strains isolated in the laboratory and which were assayed under the same conditions.

The suspension of strain CBS136973 was inoculated at approximately $10^8$ cfu/ml and the pathogens at $10^7$ cfu/ml. The pH of the apples was 3.8±0.2 and the acidity ranged between 1.6 and 2.9 g malic acid/l.

As shown in FIG. 1, the initial concentration of *E. coli* O157:H7 was 5.1 $\log_{10}$ cfu/g and it increased to 6.8 $\log_{10}$ cfu/g in the control treatment (without an antagonist). On the contrary, in the pieces coinoculated with different antagonists, there was lower growth, with reductions between 1.0 and 1.6 log units. In the case of strain CBS136973, the pathogen population after two days of storage at 20° C. was even lower than the initial one (2.4 $\log_{10}$ cfu/g), which indicates an effective reduction of 4.5 logarithmic units.

Similar results were obtained when the effectiveness of different strains was tested against *Salmonella* BAA-709 (FIG. 2), with reductions ranging between 0.3 and 1.0 log units in the case of the other antagonists and of 4.7 log units in the case of the strain CBS136973.

The increase of *Listeria innocua* population on apples not treated with an antagonist after storage at 20° C. for 2 days was 2.5 $\log_{10}$ cfu/g. In the case of some of the antagonists isolated in the laboratory, there was a significant reduction, between 1.1 and 2.2 log units, but strain CBS136973 showed much better results, with a reduction of 5.9 log units following the storage, which indicates that the population of *Listeria innocua* on apples that had been treated with strain CBS136973 was lower than 2 $\log_{10}$ cfu/g (FIG. 3).

Example 2

Effectiveness of Strain CBS136973 Against Different Foodborne Pathogens on Different Peach Varieties at 20° C.

FIGS. 4 to 6 show an example of the results obtained against strains of *Escherichia coli* O157:H7, *Salmonella choleraesuis* BAA-709 and *Listeria innocua* CECT-910, in peach, comparing the effectiveness of strain CBS136973 with other strains isolated in the laboratory and which were assayed under the same conditions.

Peaches of the "Merry O'Henry", "Tardibelle", "Roig d'Albesa", "Placido", "Royal Glory" and "Elegant Lady" varieties were used. The suspension of strain CBS136973 that was inoculated had a concentration of approximately $10^8$ cfu/ml and the pathogens were inoculated at $10^7$ cfu/ml. The pH of the peaches used was 3.6-5.3, and the acidity ranged between 2.8 and 7.8 g malic acid/l.

As shown in FIG. 4, the initial concentration of *E. coli* O157:H7 on peach was 4.9 $\log_{10}$ cfu/g, and after 2 days of storage at 20° C. it increased by approximately 3 log units in the pieces not treated with an antagonist. In the pieces inoculated with some of the isolated antagonists, the concentration of *E. coli* O157:H7 was reduced by between 1.8 and 3.0 log units, whereas the reduction with strain CBS136973 was 4.3 logarithmic units, the concentration at 2 days being even lower than the initial one, which demonstrates its great effectiveness.

FIG. 5 shows the results of the same assay, but performed with the strain of *Salmonella* BAA-709. In this case, the increase in the population after two days of storage at 20° C. was lower than that of *E. coli* O157:H7, an approximately 2.5 log increase. In general, the reductions with the other antagonists were lower, between 0.4 and 1.8 logarithmic units, but the reduction of *Salmonella* BAA-709 was greatest in those pieces of apple treated with strain CBS136973, 2.8 log units.

FIG. 6 shows the data relative to *Listeria innocua* on peach. In this FIG. 6, we may observe that the population of *Listeria innocua* in the control treatment (without an antagonist) also increased by approximately 3 log units in each piece of peach, whereas in those pieces inoculated with different antagonists isolated in the laboratory the population was lower, with reductions between 0.7 and 2.1 log units being observed. Again, the reduction obtained with strain CBS136973 was greater, 4 logarithmic units, and, once again, the final population was even lower than the initial one.

Example 3

Effectiveness of Strain CPA-7 Against Different Foodborne Pathogens on Melon at 20° C.

FIGS. 7 and 8 show an example of the results obtained against strains of *Salmonella choleraesuis* BAA-709 and *Listeria monocytogenes* LM230/3, on melon, comparing the effectiveness of strain CBS136973 with other strains isolated in the laboratory and which were assayed under the same conditions.

Melon is a fruit that has a more neutral pH and less acidity than apple and peach (pH 5.7-6.5, acidity 0.7-1.9 g citric acid/l, generally). In this case, the problem of pathogens is more significant, because the pH does not act as a barrier to the growth of foodborne pathogens. The suspension of the strain CBS136973 was inoculated at approximately $10^8$ cfu/ml and the pathogen was inoculated at $10^7$ cfu/ml.

FIG. 7 shows the results for different strains of antagonistic microorganisms, including CBS136973, against *Salmonella* on pieces of "Toad Skin" melon. In this case, the reduction values ranged between 1.5 and 3.2 log units, the greatest reduction being obtained with strain CBS136973, a total of 3.5 log units. It may be observed that the growth of *Salmonella* on melon after 2 days of storage at 20° C. was very high in the control treatment (without an antagonist), 4.2 logarithmic units, with final population being greater than $10^8$ cfu/g of product.

FIG. 8 shows the effectiveness of strain CBS136973 against the strain of *Listeria monocytogenes* LM230/3, in melon stored for 2 days at 20° C. As may be observed, in this case there is also a reduction in the pathogen with respect to the untreated control.

Example 4

Effectiveness of Strain CBS136973 Against *Escherichia coli* O157:H7 on "Golden Delicious" Apple Under Refrigeration Conditions FIG. 9 shows the result of the effectiveness of strain CBS136973 against *E. coli* O157:H7 on "Golden Delicious" apple stored at 5° C. The assay was performed by the coinoculation of 15 µl of a suspension that contained both strains, *E. coli* O157:H7 at $10^7$ cfu/ml and CBS136973 (30% transmittance, approximately $10^8$ cfu/ml).

As may be seen in the figure, at 5° C. no growth of *E. coli* O157:H7 was observed on cut apple in the control treatment; on the contrary, in the samples coinoculated with the antagonist, there was a reduction from the second day of storage and, after 7 days, the population decreased to less than 10 cfu/g.

Example 5

Effectiveness of Strain CBS136973 Against Different Foodborne Pathogens on Peach Under Refrigeration Conditions FIGS. 10 and 11 show the effectiveness of strain CBS136973 against *Escherichia coli* O157:H7 and *Salmonella* BAA-709 on peach ("Elegant Lady" and "Placido" varieties), at 5° C. and 10° C. The suspension that was inoculated had a concentration of strain CBS136973 of approximately $10^8$ cfu/ml and $10^7$ cfu/ml of pathogenic microorganisms.

As shown in FIG. 10, strain CBS136973 reduces the pathogen concentration, the reduction being greater at 5° C. than at 10° C., and it is maintained even below the detection limit after 6 days of storage.

Similar results were obtained when strain CBS136973 was used against *Salmonella* on peach of the "Placido" variety (FIG. 11). In this case, after 6 days of storage at 5° C., no *Salmonella* was detected in the pieces of cut peach, whereas the population was maintained in the treatment without an antagonist (control).

Example 6

Effectiveness of Strain CBS136973 Against *Salmonella Choleraesuis* BAA-709 on Melon Under Refrigeration Conditions FIG. 12 shows the effectiveness of strain CBS136973 against *Salmonella* BAA-709 on melon stored at 10° C. The suspension that was inoculated had a concentration of strain CBS136973 of approximately $10^8$ cfu/ml and $10^7$ cfu/ml of pathogenic microorganisms.

As shown in the figure, at 10° C. the pathogen grew in the control treatment (without an antagonist), whereas in the treatment wherein CBS136973 was applied the population remained lower, with a reduction of more than 1.5 logarithmic units from the sixth day of storage. At 5° C., under the conditions assayed, *Salmonella* was not capable of growing and the addition of strain CBS136973 did not entail any changes with respect to the control treatment.

Example 7

Effectiveness of Strain CBS136973 Applied at Different Doses Against Different Foodborne Pathogens on Golden Delicious Apple at 20° C.

Tables 4, 5 and 6 show the effectiveness of strain CBS136973 applied at different doses, and against different concentrations of the pathogens *Escherichia coli* O157:H7, *Salmonella choleraesuis* BAA-709 and *Listeria innocua* CECT-910. This effectiveness was measured in $Log_{10}$ units of growth reduction in accordance with the formula cited above.

As may be observed in the attached tables, the results show a pathogen growth reduction for concentrations of strain CBS136973 equal to or greater than the inoculated pathogen concentration.

TABLE 4

Reduction values ($Log_{10}$ units) for *Escherichia coli* O157:H7 applied at different concentrations, as a function of the dose of strain CBS124167, on "Golden Delicious" apple stored at 20° C. for 2 days.

| Dose strain CBS 124167 | Concentration of *Escherichia coli* O157:H7 inoculated (cfu/ml) | | |
|---|---|---|---|
| (cfu/ml) | $10^5$ | $10^6$ | $10^7$ |
| $10^8$ | 4.7 | 6.1 | 3.6 |
| $10^7$ | 3.8 | 3.4 | 2.0 |
| $10^6$ | 1.5 | 1.7 | 0.6 |
| $10^5$ | 0.7 | 1.6 | 0.3 |

TABLE 5

Reduction values ($Log_{10}$ units) for *Salmonella choleraesuis* BAA-709 applied at different concentrations, as a function of the dose of strain CBS124167, on "Golden Delicious" apple stored at 20° C. for 2 days.

| Dose strain CBS124167 | Concentration of *Salmonella choleraesuis* BAA-709 inoculated (cfu/ml) | | |
|---|---|---|---|
| (cfu/ml) | $10^5$ | $10^6$ | $10^7$ |
| $10^8$ | 5.4 | 3.8 | 4.5 |
| $10^7$ | 5.0 | 3.3 | 3.3 |
| $10^6$ | 3.2 | 1.9 | 1.3 |
| $10^5$ | 1.9 | 1.5 | 0.3 |

TABLE 6

Reduction values ($Log_{10}$ units) for *Listeria innocua* applied at different concentrations, as a function of the dose of strain CBS124167, on "Golden Delicious" apple stored at 20° C. for 2 days.

| Dose CBS124167 | Concentration of *Listeria innocua* inoculated (cfu/ml) | | |
|---|---|---|---|
| (cfu/ml) | $10^5$ | $10^6$ | $10^7$ |
| $10^8$ | 5.0 | 4.5 | 3.5 |
| $10^7$ | 4.2 | 3.9 | 2.2 |
| $10^6$ | 3.1 | 2.1 | 1.1 |
| $10^5$ | 2.2 | 1.3 | 0.8 |

In the case of *Salmonella* and *Listeria innocua*, inoculated in apple, the 1:1 (pathogen:antagonist) ratio is sufficient to observe reductions greater than 1.9 logarithmic units.

Of the doses assayed, the $10^8$ cfu/ml dose is the one which shows the best results for the three pathogens (reductions greater than 3.5 logarithmic units). However, the $10^7$ cfu/ml dose of strain CBS136973 is the one considered to be most adequate for commercial application, since it guarantees a minimum reduction of two logarithmic units for the three pathogens studied, regardless of the concentration of pathogenic bacteria on the fruit.

Example 8

Effectiveness of Strain CBS136973 Applied at Different Doses Against Different Foodborne Pathogens on Melon at 20° C. And 10° C.

In this example, a cocktail of strains of *Salmonella choleraesuis* (BAA-707, BAA-709, BAA-710 and BAA-711) or *Listeria monocytogenes* (CECT-4031, CECT-4032, CECT-933, CECT-940 and LM230/3) was used.

Tables 7 and 8 show the effectiveness of strain CBS136973, applied at different doses, on melon stored at 20° C., against different concentrations of the cocktail of pathogens of the genera *Salmonella* and *Listeria monocytogenes*. This effectiveness was measured in $Log_{10}$ units of growth reduction in accordance with the formula cited above.

TABLE 7

Reduction values ($Log_{10}$ units) for *Salmonella choleraesuis* applied at different concentrations, as a function of the dose of strain CBS124167, on "Toad Skin" melon stored at 20° C. for 2 days.

| Dose CBS124167 | Concentration of *Salmonella choleraesuis* inoculated (cfu/ml) | |
|---|---|---|
| (cfu/ml) | $10^5$ | $10^7$ |
| $10^8$ | 7.3 | 2.1 |
| $10^7$ | 3.7 | 0.9 |
| $10^6$ | 0.2 | 0.4 |

TABLE 8

Reduction values ($Log_{10}$ units) for *Listeria monocytogenes* applied at different concentrations, as a function of the dose of strain CBS124167, on "Toad Skin" melon stored at 20° C. for 2 days.

| Dose CBS124167 | Concentration of *Listeria monocytogenes* inoculated (cfu/ml) | |
|---|---|---|
| (cfu/ml) | $10^5$ | $10^7$ |
| $10^8$ | 5.3 | 4.9 |
| $10^7$ | 4.2 | 2.8 |
| $10^6$ | 2.1 | 1.0 |

As may be seen in the tables, in melon, the $10^7$ cfu/ml dose of strain CBS136973 shows growth reduction values of *Salmonella* and *Listeria monocytogenes*, applied at $10^5$ cfu/ml of melon, which is approximately equivalent to $10^3$ cfu/g melon, equal to or greater than 3.7 logarithmic units.

FIGS. 13 and 14 show the effectiveness of different concentrations of strain CBS136973 on melon stored at 10° C., against the aforementioned cocktails of *Salmonella choleraesuis* and *Listeria monocytogenes* applied at a concentration of $10^5$ cfu/ml.

As shown in the figures, the reduction of *Listeria monocytogenes* and *Salmonella* is greater the higher the concentration of strain CBS136973.

Assay Designed to Demonstrate the Effectiveness of Antagonistic Strain CBS136973 Against the Major Foodborne Pathogens in Fresh-Cut Fruit Under Conditions that Simulate Commercial Production.

Below we describe an example of an assay on "Golden Delicious" apple under conditions that simulate commercial production.

In this example, a cocktail of strains of *Salmonella choleraesuis* (BAA-707, BAA-709, BAA-710 and BAA-711) and a cocktail of strains of *Listeria monocytogenes* (CECT-4031, CECT-4032, CECT-933, CECT-940 and LM230/3) were used.

The whole apples were disinfected, the cores were removed and they were cut into ten slices. Subsequently, they were submerged in a bath containing the antioxidant Nature-Seal® AS1 (6%, Agricoat Ltd., Great Shefford, UK), for 2 min, under stirring, and were allowed to dry.

Once they were treated with the antioxidant, the pieces of apple were submerged in a suspension that contained the cocktail of strains of the pathogen and the antagonist, for 1 min, under stirring, simulating the application that would take place in a fruit treatment line tank. In the control treatment, the pieces of apple were submerged in a suspension that contained the cocktail of strains of the pathogen without the antagonistic strain.

Subsequently, the pieces of apple were allowed to drain, packaged (200 g) in polypropylene containers with a 500-ml capacity and sealed with a polypropylene film of the type habitually used, with a thickness of 35 μm, a permeability to $O_2$ and $CO_2$ of 3500 $cm^3/m^2*day*atm$ at 23° C., and a permeability to steam of 0.9 $g/m^2*day$ at 25° C. and 75% relative humidity. Due to respiration of the fruit and the permeability characteristics of the film to $O_2$ and $CO_2$, a passive modified atmosphere (PMA) is created inside the container. Antagonistic strain CBS136973 may be affected by this atmosphere, for which reason its effectiveness must also be demonstrated under these modified atmosphere conditions.

The pieces of apples were stored at 5° C. and at 10° C. for 15 days (estimated shelf life for this type of products). Periodically, microbiological counts were performed and different quality parameters (colour, texture, pH, acidity, soluble solids content and visual quality) were determined.

In order to obtain the suspension of strain CBS136973, production in TSB liquid medium was used and the percent transmittance (λ=420 nm) was adjusted for a concentration of the strain of $10^7$ cfu/ml.

The pathogens were inoculated in tubes containing 10 ml of TSB medium (*Salmonella choleraesuis* BAA-707, BAA-709, BAA-710 and BAA-711) or TYSEB medium (*Listeria monocytogenes* CECT-4031, CECT-4032, CECT-933, CECT-940 and LM230/3), which were incubated at 37° C. for 20-24 h. Subsequently, they were centrifuged at 8000 rpm for 10 min and the cellular precipitate was re-dissolved with 5 ml of saline solution (0.85 g/l of NaCl). By measuring the transmittance at 420 nm and a curve previously obtained in the laboratory for each of the pathogens, the estimated pathogen concentration was determined, which in the assay described was a suspension with a concentration of $10^5$ cfu/ml.

Example 9

Effectiveness of Strain CBS136973 Against Different Foodborne Pathogens on "Golden Delicious" Cut Apple Packaged at Different Temperatures Under Conditions that Simulate Commercial Conditions FIGS. 15 and 16 show the results obtained against the aforementioned cocktails of strains of *Salmonella* and *Listeria monocytogenes*, on "Golden Delicious" apple at 5° C. and 10° C.

The suspension that was inoculated by means of immersion of the pieces of apple contained a concentration of strain CBS136973 of $10^7$ cfu/ml and a concentration of $10^5$ cfu/ml of both pathogenic microorganisms.

As may be observed in the figures, strain CBS136973 was effective against *Salmonella*, especially at 10° C., where growth was observed. In the case of *Listeria monocytogenes*, growth reduction was observed at both 5° C. and 10° C.

Therefore, it may be concluded that strain CBS136973 is effective against different foodborne pathogens under conditions that simulate commercial conditions (refrigeration and passive modified atmosphere, PMA).

Moreover, it is worth noting that the application of strain CBS136973 did not affect the colour, or the texture, or the soluble solids or the acidity of the apples.

Although specific examples of the present invention have been described and represented, it is evident that a person skilled in the art may introduce variants and modifications, or replace the details with technically equivalent ones, without going beyond the scope of protection defined by the attached claims.

REFERENCES (1) Behrendt, U., Ulrich, A., Schumann, P., Erler, W., Burghardt, J., Seyfarth, W. 1999. A taxonomic study of bacteria isolated from grasses: a proposed new species *Pseudomonas graminis* sp. nov. International Journal of Systematic Bacteriology 49: 297-308.

(2) Noval, C. 1991. Comprobación del poder patógeno. En: Manual de laboratorio. Diagnóstic® de hongos, bacterias y nematodos fitopatógenos. Ed. MAPA, pp. 137-148.

(3) Peix, A.; Rivas, R., Mateos, P. F., Martinez-Molina, E., Rodriguez-Barrueco, C., Velazquez, E. 2003. *Pseudomonas rhizosphaerae* sp. nov., a novel species that actively solubilizes phosphate in vitro. International Journal of Systematic and Evolutionary Microbiology, 53: 2067-2072.

(4) Peix, A., Rivas, R., Santa-Regina, I., Mateos, P. F., Martinez-Molina, E., Rodriguez-Barrueco, C., Velazquez, E. 2004. *Pseudomonas lutea* sp. nov., a novel phosphate-solubilizing bacterium isolated from the rhizosphere of grasses. International Journal of Systematic and Evolutionary Microbiology, 54: 847-850.

(5) Abadias, M., Usall, J., Anguera, M., Solsona, C., Viñas, I. 2008. Microbiological quality of fresh, minimally-processed fruit and vegetables, and sprouts from retail establishments. International Journal of Food Microbiology, 123: 121-129.

(6) Salleh, N. A.; Rusul, G., Hassan, Z., Reezal, A., Isa, S. H. Nishibuchi, M.; Radu, S. 2003. Incidence of *Salmonella* spp. in raw vegetables in Salangor, Malaysia. Food Control 14: 475-479.

(7) Nguz, K., Shindano, J., Samapundo, S., Huyghebaert, A. 2005. Microbiological evaluation of fresh-cut organic vegetables produced in Zambia. Food Control 16: 623-628.

(8) Murray, E. G. D., Webb, R. E., Swann, M. B. R. 1926. A disease of rabbits characterized by a large mononuclear leucocytosis, caused by a hitherto undescribed *bacillus* Bacterium monocytogenes (n. sp.). J. Pathol. Bacteriol. 29: 407-439.

What is claimed is:

1. An isolated, substantially pure biological culture composition comprising a strain of the species *Pseudomonas graminis*, wherein said strain of the species *Pseudomonas graminis* is deposited under the deposit number CBS136973 at the depositary institution "Centraalbureau voor Schimmelcultures" (CBS) in Utrecht, Netherlands.

2. A method for the biocontrol of foodborne pathogenic bacteria in fruit, said method comprising the step of:
   treating the fruit with the CBS136973 strain of claim 1, wherein the CBS136973 strain is an antagonist, and wherein the fruit is intended for human consumption.

3. The method according to claim 2, wherein said fruit is fruit cut in pieces or minimally processed fruit.

4. The method according to claim 2, wherein the foodborne pathogenic bacteria are selected from the group consisting of *Salmonella* spp., *Listeria* spp., and *Escherichia coli* O157:H7 microorganisms.

5. The method according to claim 4, wherein the foodborne pathogenic bacteria are *Salmonella* spp., and
wherein the *Salmonella* spp. is of the species *Salmonella choleraesuis*.

6. The method according to claim 4, wherein the foodborne pathogenic bacteria are *Listeria* spp., and
wherein the *Listeria* spp. is of the species *Listeria monocytogenes* or *Listeria innocua*.

7. The method according to claim 2, wherein said treating step is performed at a temperature greater than about 10° C.

8. The method according to claim 7, wherein said treating step is performed at a temperature equal to or greater than about 20° C.

9. The method according to claim 2, wherein said treating step is performed under refrigeration conditions.

10. The method according to claim 2, wherein said treating step is performed in a modified atmosphere,
wherein the modified atmosphere is an atmosphere with a gas composition different from that of air.

11. The method according to claim 2, wherein said fruit is a fruit with a pH ranging between about 3 and about 7.

12. The method according to claim 11, wherein said fruit is selected from the group consisting of apple, peach, and melon.

13. A method of treating fruit, said method comprising the step of:
applying a preparation to the fruit,
wherein the preparation comprises a culture of a strain of a species *Pseudomonas graminis* deposited under the deposit number CBS136973 at the depositary institution "Centraalbureau voor Schimmelcultures (CBS)" in Utrecht, Netherlands.

14. The method according to claim 13, said method comprising the step of:
cutting the fruit into pieces prior to applying said preparation.

15. The method according to claim 13, wherein the strain of the species *Pseudomonas graminis* deposited under the deposit number CBS136973 has a specific concentration and wherein the specific concentration of strain CBS136973 in said preparation is equal to or greater than a pathogen concentration of the fruit.

16. The method according to claim 15, wherein the concentration of strain CBS136973 in said preparation is equal to or greater than about $10^5$ cfu/ml or is equal to or greater than about $10^8$ cfu/ml.

17. The method according to claim 13, said method further comprising the step of:
packaging said fruit once said preparation has been applied.

18. The method according to claim 13, said method further comprising the step of:
providing a modified atmosphere to said fruit,
wherein the modified atmosphere is an atmosphere with a gas composition different from that of air.

19. The method according to claim 13, said method further comprising the step of:
providing a refrigeration temperature to said fruit.

20. The method according to claim 13, said method further comprising the step of:
applying an antioxidant to the fruit, prior to applying said preparation.

* * * * *